(12) United States Patent
Wood et al.

(10) Patent No.: US 8,875,562 B2
(45) Date of Patent: Nov. 4, 2014

(54) FILTER AND MEMBRANE DEFECT DETECTION SYSTEM

(75) Inventors: Stewart P. Wood, Midland, MI (US); William A. Heeschen, Midland, MI (US)

(73) Assignee: Dow Global Technologies LLC, Midland, MI (US)

(*) Notice: Subject to any disclaimer, the term of this patent is extended or adjusted under 35 U.S.C. 154(b) by 321 days.

(21) Appl. No.: 13/521,543

(22) PCT Filed: Jan. 28, 2011

(86) PCT No.: PCT/US2011/022822
§ 371 (c)(1),
(2), (4) Date: Jul. 11, 2012

(87) PCT Pub. No.: WO2011/102949
PCT Pub. Date: Aug. 25, 2011

(65) Prior Publication Data
US 2012/0297863 A1    Nov. 29, 2012

Related U.S. Application Data

(60) Provisional application No. 61/305,290, filed on Feb. 17, 2010.

(51) Int. Cl.
*G01N 21/88*    (2006.01)
*G01N 21/956*   (2006.01)
*B01D 46/24*    (2006.01)

(52) U.S. Cl.
CPC ...... *G01N 21/95692* (2013.01); *B01D 46/2418* (2013.01)
USPC .......................................... 73/40.7; 356/335

(58) Field of Classification Search
CPC ................................................ G01N 21/95692
USPC .................................... 73/40.7; 356/337–343
See application file for complete search history.

(56) References Cited

U.S. PATENT DOCUMENTS 3,351,760 A    11/1967  Brown
(Continued)

FOREIGN PATENT DOCUMENTS

EP    0 445 962 A2   11/1991
EP    1 607 734 A1   12/2005
(Continued)

OTHER PUBLICATIONS

International Search Report and Written Opinion for corresponding PCT Application No. US2011/022822 filed Jan. 28, 2011; dated May 11, 2011.
(Continued)

*Primary Examiner* — Hezron E Williams
*Assistant Examiner* — Nathaniel Kolb

(57) ABSTRACT

The present invention is directed to a method of locating leaks in a substrate (30) having a first and a second surface wherein the substrate (30) is adapted for preventing the flow of a fluid, or components contained in the fluid, through the substrate (30) from the first surface to the second surface, and a system (10) useful in the method, wherein the method comprises: a) isolating the first surface from the second surface; b) creating a pressure differential between the first surface and the second surface wherein the pressure on the first surface is higher than the pressure on the second surface; c) contacting the second surface or the exit (32) of the device (11) containing the substrate (30) with a baffle (23), wherein the baffle (23) has a plurality of interconnected parts which form a pattern and the baffle (23) is of a sufficient size to cover the second surface of the substrate (30) or the fluid exit point (32) of the device the substrate (30) is disposed in and the parts of the baffle (23) create openings that particles (33) can pass through; d) exposing the surface of the baffle (23) to light from a source of diffuse light (24); e) contacting the first side of the substrate (30) with a carrying fluid containing particles (33) of a particle size that the substrate (30) is a designed to retain in the first surface of the substrate (30); f) monitoring the space above the surface of the baffles (23) for the light scattered by particles (33) that have passed through the substrate (30).

18 Claims, 4 Drawing Sheets

(56) References Cited

U.S. PATENT DOCUMENTS

| | | | |
|---|---|---|---|
| 5,076,692 | A | 12/1991 | Neukermans et al. |
| 5,102,434 | A | 4/1992 | Hijikata et al. |
| 5,411,682 | A * | 5/1995 | Nagashima ............... 264/36.15 |
| 5,424,536 | A | 6/1995 | Moriya |
| 5,463,462 | A | 10/1995 | Muto et al. |
| 5,471,298 | A | 11/1995 | Moriya |
| 5,581,017 | A | 12/1996 | Bejtlich |
| 5,790,247 | A | 8/1998 | Henley et al. |
| 6,266,137 | B1 | 7/2001 | Morinaga |
| 6,452,670 | B1 | 9/2002 | Bour et al. |
| 6,496,258 | B1 | 12/2002 | Leipertz et al. |
| 6,630,996 | B2 | 10/2003 | Rao et al. |
| 6,666,070 | B1 | 12/2003 | Hagg et al. |
| 6,731,384 | B2 | 5/2004 | Oshima et al. |
| 6,797,975 | B2 | 9/2004 | Nishiyama et al. |
| 6,803,015 | B2 | 10/2004 | Vance et al. |
| 6,809,809 | B2 | 10/2004 | Kinney et al. |
| 6,936,835 | B2 | 8/2005 | Nishiyama et al. |
| 6,998,630 | B2 | 2/2006 | Nishiyama et al. |
| 7,012,678 | B2 | 3/2006 | Enomoto et al. |
| 7,012,685 | B1 | 3/2006 | Wilson |
| 7,115,892 | B2 | 10/2006 | Nishiyama et al. |
| 7,159,599 | B2 | 1/2007 | Verbeke et al. |
| 7,256,412 | B2 | 8/2007 | Nishiyama et al. |
| 7,262,425 | B2 | 8/2007 | Nishiyama et al. |
| 7,410,528 | B2 | 8/2008 | Rae et al. |
| 7,411,207 | B2 | 8/2008 | Nishiyama et al. |
| 7,520,918 | B2 | 4/2009 | Zoeller |
| 2003/0112437 | A1 * | 6/2003 | Enomoto et al. ............... 356/402 |
| 2003/0174320 | A1 | 9/2003 | Minami et al. |
| 2004/0000186 | A1 | 1/2004 | Hagg et al. |
| 2006/0151926 | A1 * | 7/2006 | Zoeller ...................... 264/603 |
| 2006/0174695 | A1 | 8/2006 | Miyashita et al. |
| 2007/0022724 | A1 | 2/2007 | Gargano et al. |
| 2007/0132988 | A1 | 6/2007 | Gargano et al. |
| 2007/0238191 | A1 * | 10/2007 | Gargano et al. ............... 436/164 |
| 2008/0173071 | A1 * | 7/2008 | Park et al. ..................... 73/38 |
| 2009/0051909 | A1 * | 2/2009 | Kato ........................ 356/237.6 |
| 2009/0237652 | A1 * | 9/2009 | Akao et al. .................. 356/237.1 |
| 2010/0201983 | A1 * | 8/2010 | Hatano et al. ................. 356/337 |

FOREIGN PATENT DOCUMENTS

| | | | |
|---|---|---|---|
| EP | 2 103 928 | A2 | 9/2009 |
| EP | 2103928 | A2 * | 9/2009 ........... G01N 21/956 |
| JP | 09-229662 | A | 9/1997 |
| JP | 10-123067 | A | 5/1998 |
| JP | 2000-193582 | A | 7/2000 |
| WO | 2006/069006 | A2 | 6/2006 |
| WO | WO 2006069006 | A2 * | 6/2006 |
| WO | 2007/015810 | A2 | 2/2007 |
| WO | 2007/126692 | A2 | 11/2007 |
| WO | 2008/091496 | A2 | 7/2008 |

OTHER PUBLICATIONS

International Preliminary Report on Patentability for corresponding PCT Application No. US2011/022822 filed Jan. 28, 2011; dated May 25, 2012.

Second Written Opinion for corresponding PCT Application No. US2011/022822 filed Jan. 28, 2011; dated Mar. 7, 2012.

Asanuma, New Visualization and Imaging techniques for engine combustion research, Atlas Visualization, 1996, 1-43 2.

Baba et al., Analysis of transient thermal characteristic of automobile catalytic converters, Nippon Kikai Gakkai Ronbunshu B-hen, 1995, 3622-3628, 61(590), Nippon Kikai Gakkai.

Bruneaux, Liquid and vapor spray structure in high-pressure common rail diesel injection, Atomization and Sprays, IFP Rueil-Malmaison France, 2001, Abstract Only, II, (5), Begell House, Inc. New York.

Chen et al., Visualization of immiseible displacement in a three-dimensional transparent porous medium, Experiment in Fluids, 1986, 336-338, 4(6).

Elsasser et al., Mixing phenomena of fuel sprays in intake manifolds, IClass 94, proceedings of the International Conference on Liquid Atomization and Spray System, Rouen France, Jul. 1994, 758-765, Begell House, Inc. New York.

Im et al., Visualization and measurement of automotive electrostatic rotary-bell paint spray transfer process, Journal of Fluids Engineering, Jun. 2001, 237-245, 123(2), American Society of Mechanical Engineers.

Matteson ed. et al., Filtration Principles and Practices, 1987, 626, $2^{nd}$ ed., Marcel Dekker, New York.

McDonald, Scanning High-Efficiency Air Filters for Leaks Using Particle Counting Methods, Journal of the IES, Sep.-Oct. 1993, Abstract Only (full article pp. 28-37), 36(5).

Raber, Overview from Fluid Filtration; Gas, ASTM Symposium on Gas and Liquid Filtration Philadelphia, PA, Oct. 1986, ix, 1, ASTM, Baltimore, MD.

Ruiz et al., Solid Aerosol Removal Using Ceramic Filters, Separation and Purification Technology, 2000, 221-227, 19.

Talley et al., The 2-D laser sheet visualization of a pulsed hollowed cone spray: stagnant and simulated two-stroke engine environments, Atomization and Sprays, 1991, 98-112, 1(1).

Takagishi et al., Analysis of flow field in diesel fuel sprays by particle-image velocimetry, Nippon Kikai Gakkai Ronbunshu B-hen, 1999, Abstract Only (full article in Japanese pp. 1128-1132), 65(631), Nippon Kikai Gakkai.

Tsukada et al., Three-dimensional imaging of particle clusters in dilute gas-solid suspension flow, Canadian Journal of Chemical Engineering, Apr. 1997, 466-470, 75(2), Canadian Society for Chemical Engineering.

Watanabe et al., Flow visualization and measurement of torque converter stator blades using a laser sheet lighting method and a laser Doppler velocimeter, Society of Automotive Engineers, 1997, Abstract Only (full article pp. 15-25).

Yevseyev et al., Experimental investigation of a turbulent filtration flow, International Journal of Multiphase Flow, 1991, 103-118, 17(1).

Zeman et al., Latex Particle Retention by Microfilters, Microfiltration and Ultrafiltration Principles and Applications, 1996, 265-266, Marcel Dekker, Inc., New York.

* cited by examiner

FILTER AND MEMBRANE DEFECT DETECTION SYSTEM

CLAIM OF BENEFIT OF FILING DATE

The present application is a national phase application of and claims the benefit of the PCT Application US2011/022,822, filed Jan. 28, 2011 and Provisional Application 61/305,290, filed 17 Feb. 2010, the contents of which are hereby incorporated by reference in their entirety.

FIELD OF THE INVENTION

The present invention relates to system and methods useful for identifying and locating defects in substrates used to isolate particulate matter or to form a barrier, such as barrier films, membranes or filters.

BACKGROUND

Substrates that are designed to isolate particulate matter or to form a barrier from fluids, gasses, light, and solids are well known in the art. Included in such substrates are barrier films that are designed to prevent the transmission of a particular fluid across the barrier. Examples of fluids for which barrier films are utilized include oxygen and water. Typically, the barrier film is located between a source of the fluid and an object or region to be protected from the fluid. Another class of such substrates is membrane systems. Typically these membrane systems utilize a barrier that is capable of separating mixtures of fluids or separating solids or particulates from a fluid. One class of membranes separate a mixture of different gaseous materials into components, for instance oxygen from nitrogen or carbon dioxide from an air stream. Another class of membrane systems is designed to separate particulate matter or entrained or dissolved chemical species from a liquid. One example includes a reverse osmosis membrane designed to remote salt from brackish or salt water. Another example includes an ultrafiltration membrane which can remove higher molecular weight organic compounds from a liquid. Another class of substrates is wall flow filters. Wall flow filters are typically ceramic based and separate particulates from fluids based on size. A common design of a wall flow filter comprises a shaped ceramic article with flow passages that extend through the article in one direction. Wall flow filters have in one direction a series of walls that define flow passages generally arranged such that the walls and flow passages are disposed parallel to one another and the walls and passages extend through the shaped ceramic article. In the direction perpendicular to the walls and flow passages the wall flow filters generally demonstrate a consistent cross-sectional shape. The cross sectional shape can be any shape which is suitable for the intended use of the wall flow filter. The cross sectional shape can be circular, oval, square, rectangular, polyhedral or a shape defined by an assembly of square, rectangular or polyhedral shaped parts. In some embodiments, the wall flow filter exhibits two faces at each end having the desired cross-sectional shape and the flow passages are perpendicular to the faces of the filter and extend from one end or face to the other end or face. Often, this arrangement is referred to as a honeycomb design because each end of the filter looks similar to a honeycomb. In a preferred embodiment the wall flow filter has a cylindrical shape having a circular or oval cross sectional shape. In another preferred embodiment, the wall flow filters comprise a plurality of individually formed parts that are assembled together to form a desired cross section in the direction perpendicular to the direction of the flow passages. In this last instance the cross section of the wall flow filter comprises an assembly of the cross section of the parts used to prepare the wall flow filter and can be engineered to have any desired shape. Wall flow filters often are arranged having a plurality of walls defining a plurality of flow passages. In wall flow filters at one end every other flow passage is plugged such that the fluids cannot pass through the end of the plugged flow passage. At the other end the remaining passages are plugged in a similar manner. The arrangement results in a structure such that each flow passage is open at one end and plugged at the opposite end. Each flow passage is surrounded by passages that are plugged at the opposite end from which it is plugged. In order to separate particulates from a fluid stream, the fluid stream is introduced through one end of the filter into the flow passages in that end. Because the other ends of the flow passages are plugged the fluid can only exit the filter through the porous walls of the flow passage and into flow passages adjacent to the flow passage into which the fluid is introduced. The flow passages into which the fluid passes are open at the opposite end from fluid introduction. Typically, a pressure differential is maintained between the flow passage into which the fluid is initially introduced and the flow passages adjacent thereto to drive the fluid through the flow passage walls. The particulate matter contained in the fluid which is of a size greater than the pores in the walls of the flow passage is retained on the wall of the flow passage into which the fluid is introduced. The fluid flowing out of the opposite end of the filter is substantially free of particulates of a size greater than the pores found in the walls of the flow passages. In a preferred embodiment the manufacture of the wall flow filters is adapted to produce walls with relatively uniform pores to facilitate the desired separation. The design and manufacture of ceramic wall flow filters is well known in the art and not subject of this invention. Substrates that can be used as films or membranes which are substantially flat and the fluids to be separated or purified are contacted with one side of the film and either prevented from passing through the film or the desired fluid is passed through the film and collected on the opposite side and the undesired material is retained on the original surface of contact. In other embodiments, the substrate is arranged in another way in a device having an inlet for feeding the fluid to be separated and an exit for recovering the purified fluid. This exit may be remote from the actual separating species. Examples of structures of this type are wall flow filters, hollow fiber membranes and spiral wound membranes systems.

In the devices in which these barrier films, membranes or filters are incorporated defects in fabrication can allow undesired fluids or particulate matter to flow into the recovered fluid. Also if the barrier films, membranes or filters have defects undesired fluids or particulate matter can pass through the barrier films, membranes or filters. Such defects render them unsuitable for use. Thus it is desired to identify defective barrier films, membranes or filters and systems containing them which due to defects cannot effectively utilize the barrier properties or perform the separation required. Methods and apparatus for identifying such defects in wall flow filters are known in the art, see Kato, US 2009/0051909; Gargano et al US 2007/0022724; Gargano et al US 2007/0238191; Hijikata et al U.S. Pat. No. 5,102,434; and Zoeller, III U.S. Pat. No. 7,520,918; all incorporated herein by reference. All of these disclosed systems and methods require the use of highly directional light sources, lasers, wherein a very thin sheet of light is used to locate the particulate matter exiting the wall flow filters. These methods require that the thin sheet of light be located at a distance from the surface of the wall flow filter.

There is still a need for systems and methods of identifying and locating defects in barrier films, membranes, filters and systems containing the barrier films, membranes or filters. Systems and methods which operate in a non-destructive fashion, which identify and locate the defects in a timely manner as part of the manufacturing process and which can identify the location of the defect in the barrier films, membranes or filters or at the exit from the system containing the barrier films, membranes or filters are desired.

SUMMARY OF THE INVENTION

The present invention relates to a system for locating defects in a substrate adapted to separate components of fluids or solids from fluids. Such substrate having at least two surfaces, a first and a second surface, which are isolated from one another and wherein the substrates or systems containing the substrates have an exit point for fluids passing through the substrate. The system of the invention comprises: a) a particle source capable of generating particles of a controlled size which is greater than the size of particles which the substrate is adapted to retain on the first surface; b) a system for creating a pressure differential between the first and the second surface of the substrate; c) a diffuse source of light; d) a baffle having a plurality of flow passages or openings that particles can pass through; e) a closed flow path from the particle generator to the first surface of the substrate; wherein the light source is directed, in the direction of the second surface of the substrate or the exit of the device containing the substrate, the angle of the direction of the light from the light source and the pattern and size of the interconnected parts of the baffle are selected such that no detectable light from the light source directly contacts the first surface of the substrate or the exit of the substrate. No detectable light as used in this context means that no light from the light source which impinges on the surface of the substrate or the exit of the device containing the substrate interferes with monitoring the presence of particulate matter exiting the surface of the substrate or the exit of the device containing the substrate.

In another embodiment the invention relates to a method of identifying and/or locating defects in a substrate comprising a wall having a first surface and a second surface located on the opposite side of the wall from the first surface which method comprises placing a substrate in a system as described herein such that first surface of the wall and the second surface of the wall are isolated from one another; contacting a fluid containing particles of a size the substrate is designed to retain on the first surface under conditions that the pressure on the first surface is greater than the pressure on the second surface; directing the light of the diffuse light source onto the baffle and monitoring the surface of the baffle for particles, which scatter light from the light source, passing through the baffle. In a preferred embodiment the surface of the baffle is monitored using an imaging system.

In another embodiment, the invention relates to a method of locating leaks in a substrate, having a first and a second surface wherein the substrate is adapted for preventing the flow of a fluid, or components contained in the fluid, through the substrate from the first surface to the second surface, wherein the process comprises: a) isolating the first surface from the second surface; b) creating a pressure differential between the first surface and the second surface wherein the pressure on the first surface is higher than the pressure on the second surface; c) contacting the second surface or the exit of the device containing the substrate with a baffle, wherein the baffle has a plurality flow passages and the baffle is of a sufficient size to cover the second surface of the substrate or the fluid exit point of the device the substrate is disposed in and the flow passages of the baffle provide openings that particles can pass through; d) exposing the surface of the baffle to light from a source of diffuse light; e) contacting the first side of the substrate with a carrying fluid containing particles of a particle size that the substrate is a designed to retain in the first surface of the substrate; f) monitoring the space immediately above surface of the baffle for the light scattered by particles that have passed through the substrate and the baffles.

It should be appreciated that the above referenced aspects and examples are non-limiting, as others exist within the present invention, as shown and described herein. The systems and methods of the invention allow the use of a standard light source, which is a source of diffuse light as opposed to a highly directional light source (non-diffuse light source) such as a laser. The systems and methods of the invention allow the identification and location of defects in substrates and systems containing the substrates in a non-destructive fashion, which under certain circumstances facilitate repair of the substrate or system containing the substrate. The system and methods of the invention allow a manufacturer to see particulate matter exiting the substrate or the device containing the substrate close to the substrate or the exit, for instance within 1 mm of the surface of the substrate or the exit of the device containing the substrate.

DETAILED DESCRIPTION OF THE PREFERRED EMBODIMENT

Figure 1:
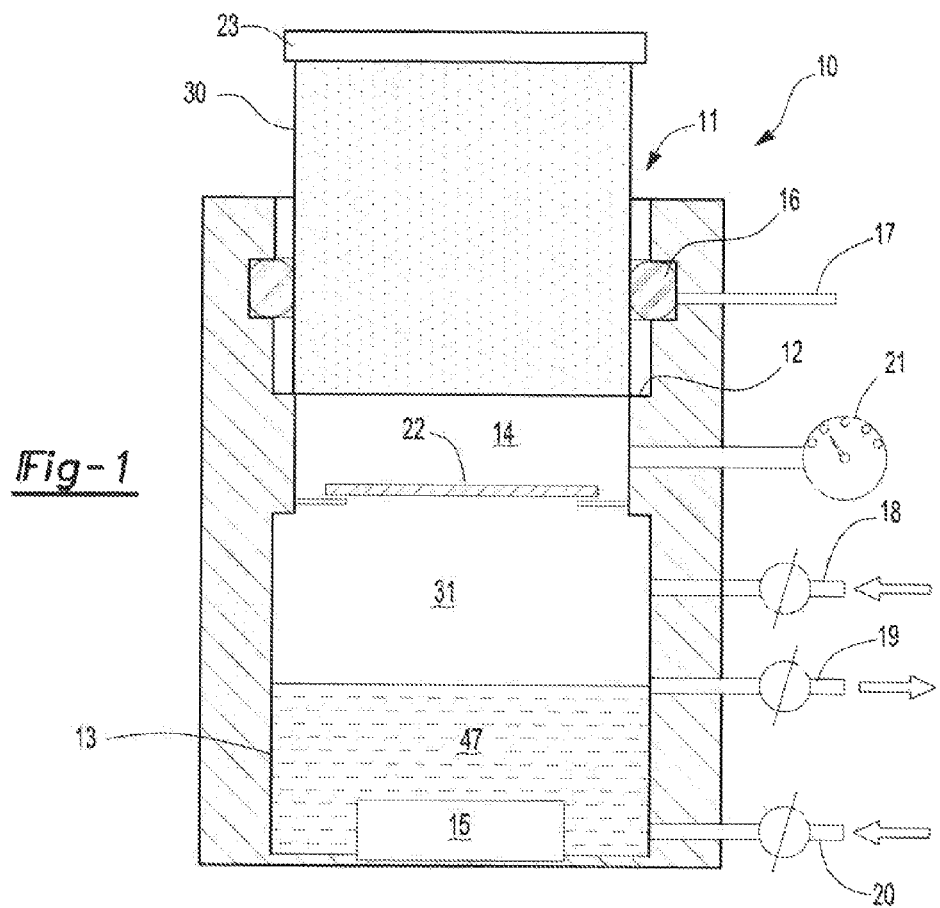
FIG. 1 is a view of a wall flow filter located in the holder of a system of the invention.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the description contained herein, but should instead be determined with reference to the appended claims, along with the full scope of equivalents to which such claims are entitled. Other combinations are also possible as will be gleaned from the following claims, which are also hereby incorporated by reference into this written description.

The system and method of the invention relate to locating defects in substrates wherein the substrates comprise a barrier layer or a filtration layer. Preferably, substrate as used herein refers to a material that has inherent thickness, that is a wall, and two surfaces, a first and a second surface, wherein the surfaces are capable of being separated from another by material between the two surfaces. Capable of being separated from one another means the two surfaces can be arranged such that a fluid can be forced to pass through the wall of the substrate to transport it from the first surface to the second surface. Barrier as used herein refers to the inherent property of preventing a fluid, particle, or light from passing through the barrier layer. A filtration layer refers to a material that is designed to separate components of a fluid stream or components contained in a fluid stream from the fluid stream. The filtration layer can perform the separation either based on the differences of solubility and diffusivity of two fluids in the material from which the filtration layer is composed, or based on the size of the pores in the filtration layer. Typically, where a filtration layer is designed to separate materials by size, the pore size is carefully designed. The substrate can take any form which allows the first surface and the second surface to be isolated from one another in order to force fluids to pass through the substrate. Example of such forms include wall flow filters, flat sheets, films, hollow fibers, spiral wound membrane systems and the like. During use a substrate may be exposed or may be disposed within a system. Wherein the substrate is used in a system, the system typically is designed to isolate the first surface from the second surface. Such a system generally has an inlet for feeding a fluid mixture to the first surface of the substrate and an exit for removing the portion of the fluid which passes through the wall of the substrate. In the embodiment wherein the substrate is a wall flow filter as described hereinbefore, the wall flow filter has two faces, ends, which preferably are planar in a direction perpendicular to the direction of the flow passages. The flow passages are preferably oriented perpendicular to the plane of the two faces of the wall flow filter. At one end of the wall flow filter are openings of the flow passages. The end of the flow passage opposite to the open end is plugged with a material which is capable of preventing the flow of fluid out of the flow passage. Every open passage is surrounded by plugged flow passages. In the same manner, every plugged flow passage is surrounded by open flow passages. At the other end, the plugged passages are open and the open passages are plugged. The result of this design is that when a fluid is introduced at the inlet end and brought into contact with the first surface of the substrate and there is a higher pressure on the first surface of the substrate than on the second surface of the substrate, the fluid passes through the walls of the substrate from the first surface to the second surface. To the extent that the fluid contains materials of a size larger than the pores the materials are retained on the first surface of the substrate. As used herein separating components of a fluid means separating different parts of the fluid based on either size or solubility and diffusivity of the components through the substrate. As used herein the first surface of the substrate is the surface of the flow passages in contact with the inlet. As used herein the second surface of the substrate is the surface of the flow passages in communication with the exit. Pore size refers to the largest size of openings contained in the substrate. Typically, substrates are engineered to have a controlled largest size such that the substrate is capable of separating particulate matter of a certain size from a fluid.

Defects in a substrate mean that there are openings in the substrate that allow fluid components to pass through the substrate which the substrate is designed to prevent from passing through the substrate. Typically, the defects comprise holes or cracks in the substrate that are larger than the desired pore size. These defects allow the material to pass through the substrate that was intended to be retained on the first surface of the substrate. Such defects render the substrate ineffective. In the context of a system containing the substrate, the defects typically result in a failure to isolate the first surface of the substrate from the second surface of the substrate thus allowing undesired materials to pass directly from the inlet to the exit. Identification of defective substrates and/or systems allows the manufacturer to either correct the defects or prevent the sale of defective systems.

Generally, the invention comprises systems for locating defects in a substrate adapted to separate fluids or components from fluids, the substrate having at least two surfaces, a first and a second surface, which are isolated from one another and wherein the substrates or systems containing the substrates have an exit point for fluids passing through the substrate, the system comprising: a) a particle source capable of generating particles of a controlled size which is greater than the size of particles which the substrate is adapted to pass from the first surface to the second surface; b) a system for creating a pressure differential between the first and the second surface of the substrate; c) a source of diffused light; d) a baffle having a plurality of interconnected parts which form a pattern wherein the baffle is of a sufficient size to cover the second surface or the fluid exit point of the device containing the substrate, wherein the interconnected parts create openings that particles can pass through; e) a closed flow path from the particle generator to the first surface of the substrate; wherein the light source delivers light to the second surface of the substrate or the exit of the device containing the substrate, the angle of the direction of the light from the light source and the pattern and size of the interconnected parts of the baffle are selected such that any light from the light source which directly contacts the first surface of the substrate or the exit of the device containing the substrate and is reflected by the first surface of the substrate or the exit of the device containing the substrate does not interfere with the ability to monitor the light scattered by any particles passing through the substrate or exiting the device containing the substrate. It is desired that any light scattered by the substrate or the exit of the device containing the substrate, whether it is from the diffuse light source or ambient light, be low in intensity so that it goes undetected by the system adapted to detect light reflected by the exiting particles. The light scattered by the particles passing through the defect in the substrate must be greater in intensity than any light scattered off of the substrate. Exit point as used herein refers to an outlet for fluids which have passed through the wall of the substrate from the first surface to the second surface, which exit point is used to remove the fluids passed from the vicinity of the second surface of the substrate. In the context of a wall flow filter, the substrate refers to the walls of the flow passages and the exit of the device refers to the end of the wall flow filter in communication with the flow passages in communication with the second surface of the substrate.

The system of the invention contains a source of particles. The particles may comprise any particles which are larger in size than the designed pores of the substrate and which can scatter light when they pass from the exit point of the substrate and through the incident light or system. The particles utilized need to be capable of being diffused in a fluid. Fluid as used herein is a material that flows when subjected to the pressure differential. Preferably the fluids used herein are in the liquid or gaseous state and more preferably are in the gaseous state. The particles can be solids, liquids or gases provided the particles scatter light, more preferably they are solid or liquid. In general terms, the source of particles is a particle generator which is any device or system that can form particles of the desired size having the desired properties. In one embodiment the particles are formed from a liquid material. The particulate fluid is preferably a suspension of fine drops of liquid in air, that is a mist or a fog. The particulate generator in this embodiment is a device that generates a fine particle mist, such as a sprayer, nebulizer, atomizer, and the like. The liquid used to form the particles can be any liquid that can be formed into particles which scatter light. Preferable liquids which can be used include water, glycols and the like, with water being preferred. In another embodiment, the particles can be smoke, soot, incense, wheat flour and the like. Any system that generates such particles can be used as the particle generator. The size of the particles used is dependent on the pore size of the substrate and the size of the defect of interest. There are practical constraints on the size of the particles. The lower limit on the size of the particles is the smallest size of particles that scatter light in a detectable manner. Thus the lowest useful particle size is the lowest particle size that scatters light when particles of that size exit the substrate or device containing the substrate and come into contact with light from the non-diffuse light source. The upper limit on particle sizes useful is based on the ability to transport the particles in a carrier. If the particles are too large they cannot be transported in a carrier fluid. The size of the particles is preferably about 0.1 micrometers or greater, more preferably about 0.5 micrometers or greater, even more preferably about 1.0 micrometers or greater and most preferably about 5 micrometers or greater. In the embodiment wherein the substrate is a wall flow filter, the sue of the particles is about 100 micrometers or less, more preferably about 20 micrometers or less and most preferably about 15 micrometers or less.

Preferably, the particles are dispersed in a carrying fluid. The carrying fluid is determined according to the nature of the substrate and the materials the substrate is designed to separate. Preferably, the fluid is a gas. The particles can be dispersed in any gas that does not harm the substrate. The gas can be air, oxygen, nitrogen, carbon dioxide or an inert gas. Preferably, the gas is air. Preferably, the air is filtered to remove entrained particulate matter. In some embodiments, the system can comprise a source of gas. Any source of gas which is capable of transporting the particles and which does not harm the substrate or the system in which it is disposed may be used. The source of gas can be a pressurized tank of the desired gas, a blower, preferably with a filter for the gas or a combination thereof.

The system may further comprise a device for dispersing the particles into the carrying fluid. Any system that facilitates dispersal of the particles into the carrying fluid that facilitates contacting the particles with the substrate may be used. Such dispersal devices include a sprayer, a mixing chamber containing an impeller or air jet, a static mixer, an ultrasonic atomizer or a recirculator. In one embodiment, the dispersal device is a chamber into which the particles are introduced which further contains a blower which disperses the particles into air, and preferably further contains an impeller.

The system utilizes a device for creating a pressure differential across the wall of the substrate. The pressure differential is between the first surface of the substrate and the second surface of the substrate, in particular the pressure on the first surface is higher than the pressure on the second surface of the substrate. Any device which, creates the pressure differential may be used. In one embodiment, a device which increases the pressure an the first surface of the substrate may be used. Examples of devices which increase pressure on the first surface of the substrate include gas blowers, pressurized gas tanks, a gas compressor and combinations thereof. In another embodiment, a device which reduces the pressure on the second surface of the substrate may be utilized. In a preferred embodiment, a vacuum is created on the region in contact with the second surface. Examples of means for creating a vacuum in the region in contact with the second surface of the substrate include a vacuum pump, a molecular diffusion pump, a syringe pump, or a combination thereof. The pressure differential is chosen such that the carrying fluid is driven through the wall of the substrate from the first surface to the second surface and carried away from the second surface. The particular pressure differential needed is dependent on the nature of the substrate, the nature of transport of the fluid through the substrate, the nature of the fluid and the size of the pores, where present, in the substrate. Any pressure differential which causes the carrying fluid to pass through the wall of the substrate from the first surface to the second surface may be utilized. In a preferred embodiment, the pressure differential is about 1 pascal or greater, more preferably about 4 pascals or greater, and most preferably about 6 pascals or greater. In a preferred embodiment, the pressure differential is about 100 pascals or less, more preferably about 50 pascals or less, and most preferably about 30 pascals or less.

The source of light used in system can be any source of diffused light. As used herein diffuse light is light that is not highly directional. Directional light means the light has a measured directivity. The level of directivity is less than that required in prior art. Any light source that provides diffused light may be used as the source of light in the system. Examples of such sources of light include incandescent light bulbs, fluorescent light sources, light emitting diodes and combinations thereof. The light source can comprise one or more individual light sources. In a preferred embodiment, the source of light is a plurality or array of individual light sources. In a more preferred embodiment, the light source is an array of light emitting diodes. Preferably the light source delivers a divergent cone of light, a plane of light, or a beam of light. In the case of the beam of light the beam is scanned over the substrate exit so as to allow complete evaluation of the substrate exit. More preferably, the light source would be a divergent plane of light or scanned beam of light. The directivity of the light is defined by the degree of dispersion of the light at a given distance from the light source. The degree of dispersion is defined by the diameter of the beam or cone of light or the thickness of the plane of light. Directivity is the directional characteristic of a light source. All light sources exhibit directionality. In the case of this invention, directivity is characterized by the diameter of a beam of light, the diameter of a cone of light, or the thickness of a plane of light at a distance of one meter from the light source. A typical beam of laser light is considered as highly directional, non-diffuse, since its diameter is very small when measured at or near the laser exit. A plane of light that is formed by dispersing a laser beam in one dimension can also be considered highly directional in one dimension, i.e. the plane thickness, since the plane thickness will remain the same as the thickness of the original light beam independent of the degree of dispersion of the beam in the other direction. The directionality of the non-laser based light sources utilized in this invention is less than that of a typical laser. To differentiate the overall magnitude of the directionality of various light sources a length measurement is used. The diameter of a beam of light, the diameter of a cone of light, or the thickness of a plane of light at a distance of one meter from the light source is determined using a light meter. The light meter, which has a 3 millimeter working aperture placed onto the active surface thus providing an opening to the active surface, is scanned across the center of the beam or cone of light or the thickness of the plane of light to obtain a spatial light intensity distribution. The beam or cone diameter or the plane thickness is measured at half the maximum intensity of the beam, cone, or plane spatial light distribution. In the preferred embodiment the beam or cone diameter or plane thickness, at a distance of 1 meter from the source, is about 4 mm or greater, more preferably about greater 6 mm or greater, and most preferably about 20 mm or greater. Preferably the beam or cone diameter or plane thickness, at a distance of 1 meter from the source, is about 1000 mm or less, more preferably about 200 mm or less, and most preferably about 100 mm less than. The light source can generate a broad spectrum light or a monochromatic light. Monochromatic light, light of a single color, having a narrow wavelength band, is preferred. Light of a single color is preferred because it enhances the image capture by an image capturing system. Use of monochromatic light allows more effective filtering of unwanted stray light in the capturing of the images. The color chosen is preferably violet, green, red or blue, with red most preferred.

The system of the invention includes a baffle which is disposed at or near the second surface of the substrate or at the exit of the system. The closer the baffle is to the second surface of the substrate, the easier it is to locate any defects in the substrate. The baffle preferably is large enough to cover the entire area of the second surface of the substrate or the exit of the device in which the substrate is located. In the embodiment where the substrate is in film or sheet form, the baffle preferably is of a size to cover the entire sheet or film. The shape in the direction of the plane parallel to the plane of the substrate or exit of the device containing the substrate is not critical as long as it covers the surface area of the substrate or exit. In a preferred embodiment, the baffles shape in the plans parallel to the plane of the substrate or exit of the device containing the substrate conforms to the shape of the substrate or the exit of the device containing the substrate. In the embodiment wherein the substrate is a wall flow filter, the baffle is of a size which is at least the same size and shape of the second face of the filter, which is the face from which the fluid exits the filter. The baffle functions to allow fluids including particles to travel away from the surface of the substrate and to prevent light from the light source from directly contacting the surface of the substrate or the exit of the device containing the substrate or to prevent the substrate of the exit of the device containing the substrate from reflecting light in a manner which interferes in the identification of defects in the substrate or device containing the substrate. The baffle further comprises a plurality of openings adapted to allow any particles which exit the substrate of device containing the substrate to pass through the holes in the baffle. The baffle comprises a border which defines the size and shape of the baffle. Any structure which provides appropriate passage of the carrier fluid and particles therethrough may be used. In one embodiment the baffle may be a unitary structure with holes formed in the structure. Such unitary structure can be molded into the desired shape and can be prepared from any material capable of being formed or molded into the desired shape, such as metal, plastic and ceramics. In one embodiment the baffle can be a relatively thin wall flow filter placed upon the surface of the wall flow filter being tested. In one preferred embodiment, the wall flow filter utilized as a baffle is relatively thin in the direction perpendicular to the flow passages. In one embodiment, baffle having a plurality of interconnected parts which form a pattern wherein the baffle is of a sufficient size to cover the second surface or the fluid exit point of the substrate and the interconnected parts create openings that particles can pass through. In one embodiment, the passages in the baffle may be formed by a plurality of parts which interconnect to form a mesh or screen. The baffle is adapted to prevent the diffuse light from directly contacting, or reflecting from in a manner which prevents identification of defects, the surface of the substrate or exit of the device containing the substrate. The passages in the baffle or openings between the parts need to be sufficient to allow the fluid and particles passing through the substrate to flow away from the substrate or exit without substantial interference. The shape and dimensions of the passages or parts are chosen to achieve these stated objectives. The thickness in the plane parallel to the plane of the substrate or exit from device containing the substrate, for wall flow filters, the exit face, is selected to minimize the surface area covered by the structure defining the passages or the parts. In the direction perpendicular to the substrate or exit from the substrate, for wall flow filters the exit face, the thickness is chosen so as to prevent the light from the diffuse light source from contacting, or reflecting from in a manner which interferes with detection of defects, the substrate or exit of the device containing the substrate, for wall flow filters the exit face, and to be as thin as possible so that the location of any particles exiting can be identified as close as possible to the surface of the substrate or the exit. The plurality of parts defining the openings in a baffle can comprise any shape which meets these objectives, including wire, thin strips with the thickest dimension perpendicular to the plane of the substrate or exit from device containing the substrate, for wall flow filters the exit face or combinations thereof. The parts are interconnected to form a pattern wherein the parts form a plurality of openings. The number pattern and the plurality of openings are arranged to allow the fluid and particles to leave the vicinity of the plane of the substrate or exit from device containing the substrate, for wall flow filters the exit face. Preferably, the thickness in the direction perpendicular to the plane of the substrate or exit from device containing the substrate, for wall flow filters the exit face, is preferably about 100 mm or less, more preferably 10 mm or less and most preferably 0.2 mm or less. The minimum thickness is chosen such that the baffle has structural integrity and prevents light from contacting, or reflecting in a manner which interferes with detecting particles exiting the substrate or exit from device containing the substrate, for wall flow filters the exit face. Preferably, the thickness in the direction perpendicular to the plane of the substrate or exit from device containing the substrate, for wall flow filters the exit face, is preferably about 0.01 mm or greater and most preferably 0.04 mm or greater. The openings which form the flow passages in the baffle are preferably of a size of about 0.05 mm or greater, more preferably about 0.07 mm or greater and most preferably about 0.1 mm or greater. The openings which form the flow passages in the baffle are preferably of a size of about 5.0 mm or less, more preferably about 3 mm or less and most preferably about 0.3 mm or less. In a preferred embodiment, the baffle comprises a metallic, plastic, or cloth mesh, the flow passages are defined by interconnected wires or threads. In a preferred embodiment the baffle does not reflect the diffuse light. The baffle is preferably black in color and has a flat matte finish.

The flow path is adapted to transport the carrier fluid containing particles from the source of particles and source of carrier fluid to the first surface of the substrate or in the inlet of a device containing the substrate, in the embodiment wherein the substrate is a wall flow filter to the inlet face of the filter. The flow path can be of any shape and manufactured from any material which facilitates introduction of the fluid containing particles to the surface of the substrate. In a preferred embodiment, the flow path creates a closed environment which can be pressurized to create a pressure differential. In one embodiment, the flow path creates a closed chamber, in another embodiment the flow path can be connected to a device for mixing the carrier fluid and the particles and collectively these parts can form a sealed chamber which is capable of being pressurized. The closed chamber can contain a pressure sensor and or regulator, an inlet for introduction of particles, an inlet for introduction of a fluid wherein the fluid may be pressurized, a blower to create pressure, or an inlet from a blower to create pressure, a gas compressor or any combination thereof. In a preferred embodiment, a seal is located between the flow path and the substrate or device containing the substrate. The seal is adapted to seal between the flow path and the substrate or the device containing the substrate and to maintain pressure of the chamber where the chamber is pressurized. Any seal that performs this function may be utilized. The seal may be an elastomeric material and in one embodiment may comprise a gas filled bladder of a flexible or elastomeric material which is capable of conforming to the substrate or device containing the substrate. The flow path and the chamber perform the additional function of isolating the first surface of the substrate from the second surface of the substrate.

Figure 7:
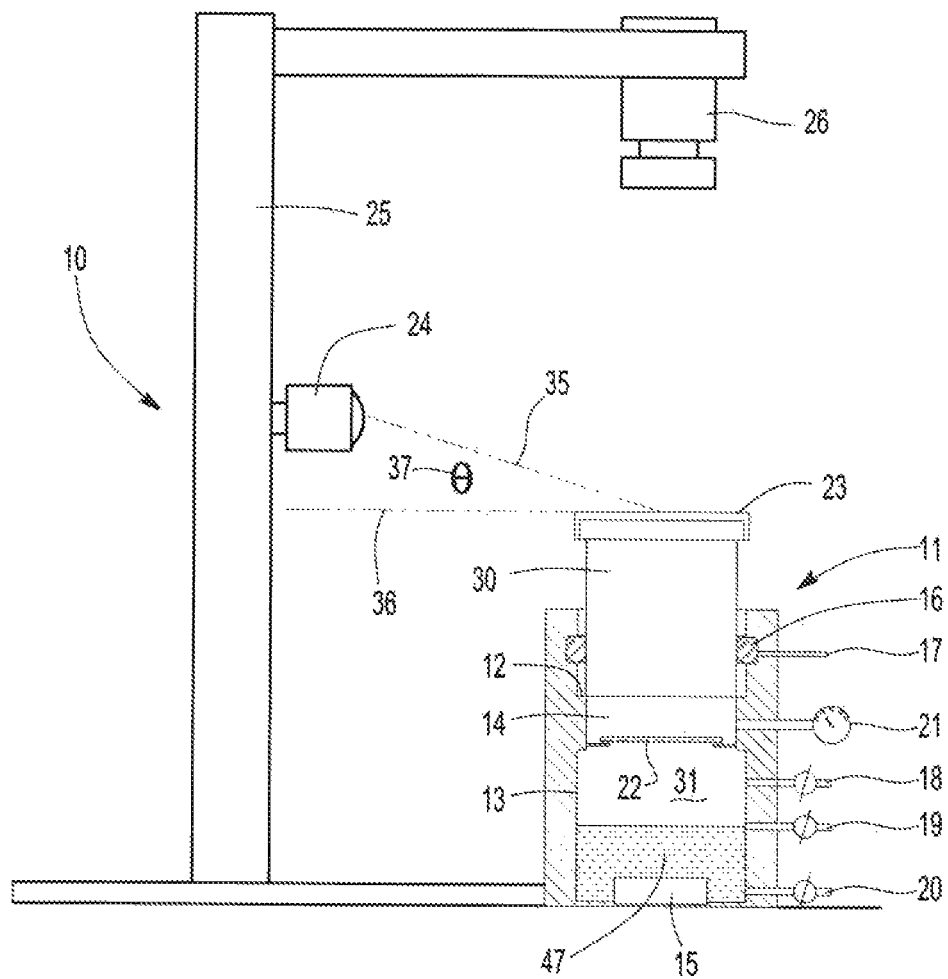
FIG. 7 is a view of a wall flow filter in a defect testing device which shows the angle of the central vector of diffuse light on the center of the baffle compared to the plane of the surface of the baffle.

The direction of the center vector of the diffuse light and the size and design of the baffle are selected to prevent the diffuse light from directly contacting the surface of the substrate or exit of the device containing the substrate, such as the exit face of a wall flow filter, or from reflecting from the surface of the substrate in a manner which interferes with monitoring particles passing through the baffle. Directly contacting means that light rays flow directly from the light source to the object. Center vector refers to the vector of light at the center of the light projected by the light source. The light is diffuse and the most intense light rays are projected in towards the exit of the device containing the substrate. The central vector is used to define the relationship of the substrate, the baffle and the light source. The direction of the central vector cannot be perpendicular to the plane of the substrate or exit from the device containing the substrate. With respect to wall flow filters, the central vector cannot be perpendicular to the plane of the exit face and in the same direction of the vector of the flow of the flow passages. In this alignment, the light rays from the diffuse light source will contact the surface of the substrate or the exit from the device containing the substrate, or the face of the exit of a wall flow filter, and the light rays will reflect therefrom in a manner which prevents detection of the particles exiting. This reflected light interferes with the identification of and location of defects. Therefore the angle between the vector of the center of the light generated by the diffuse light source when directed at the center of the face of the baffle and the plane of the substrate or the exit from the device containing the substrate, exit face of a wall flow filter, is significantly less than 90 degrees. Preferably, the angle is 85 degrees or less, and more preferably 50 degrees or less and most preferably 30 degrees or less. Preferably the angle is 0 degrees or greater and more preferably 2 degrees or greater. The center of the face of the baffle is the geometric center of the face of the baffle. For irregular shapes the center can be estimated. The thickness of the baffle, the size of the openings and the angle discussed above are interdependent. When the openings are smaller and the thickness is greater, the angle can be greater. When the openings are larger or the baffle thinner the angle needs to be smaller, FIG. 7 shows the relevant angle.

The surface of the substrate or the exit of the device containing the substrate with the baffle disposed near or adjacent to the exit or substrate is monitored for exiting particles. The particles exiting scatter light and the scattered light is visible to the naked eye. Thus the monitoring can be performed manually. The system preferably comprises an image capturing system to capture and preferably save images of the light scattered by those particles exiting from the device. Any imaging system which allows the capture of images of particles passing through the baffle may be used. The imaging capturing system preferably records the images in a known recording medium in a manner such that the images can be examined in order to locate the defect in the substrate, quantitatively describe the defect in a number of ways such as the magnitude of the defect or the number of defects present or the magnitude of defects per area of the number of defects per area or any combination thereof. The imaging device may be an analog or digital device. The imaging system can comprise an imaging device which captures a series of static or still images or it may capture a real time video image. The imaging system is preferably connected to computer system such that images can be stored and/or further processed to determine the location of the defect in the substrate, quantitatively describe the defect in a number of ways, such as the magnitude of defects per area, the number of defects per area or any combination thereof. These operations can be performed by visual inspection or by computer based image processing and image analysis. In another preferred embodiment, the imaging system includes a monitor which shows the image or the image processed in a manner such that the location of the defect is identified. The image capturing system can be adjusted to filter out unwanted images or light wavelengths. Where the diffuse light source is a monochromatic light source the image capturing system can be adjusted to filter out all light except the monochromatic light wavelength band utilized by the diffuse light source.

In a preferred embodiment a lens is disposed between the diffuse light source and the baffle near or adjacent to the substrate or the exit of the system containing the substrate. The lens is adapted to focus the majority of the diffuse light on the surface of the baffle. The lens does not convert the light to highly directional light. The lens is utilized to maximize utilization of the light from the diffuse light source. One skilled in the art of optics with knowledge of the set up of the system is capable of choosing and recommending an appropriate lens for a particular system.

The parts of the system of the invention can be separate modules which are arranged to function as described herein. Alternatively, a portion of or all of the parts can be integrated and held in place by a support structure. Such a support structure can hold and align appropriately some or all of the parts. The system of the invention and in a preferred embodiment the support structure, further comprises a holder for the substrate or the device containing the substrate. The holder along with the flow path preferably cooperates to isolate the first surface from the second surface. The holder may further comprise a known restraining device for restraining the substrate or device containing the substrate to hold it in an appropriate location. Such restraining devices are well known to a skilled artisan.

The system of the invention can be incorporated into a manufacturing system or plant. As part of the manufacturing system it is contemplated that the substrate or device can be manually inserted into the system of the invention. Alternatively, the device or substrate can be placed into the system utilizing a robot. The robot can be part of the system of the invention or can be separate and adapted to work with the system of the invention. Robotic systems which can be used with the system of the invention are well known to one skilled in the art.

In another embodiment the invention relates to a method of identifying and/or locating defects in a substrate comprising a wall having a first surface and a second surface located on the opposite side of the wall from the first surface which comprises placing a substrate in a system as described herein such that first surface of the wall and the second surface of the wall are isolated from one another; contacting a fluid containing a particles of a size the substrate is designed to retain on the first surface under conditions such that the pressure on the first surface is greater than the pressure on the second surface; directing the diffuse light of the diffuse light source onto the baffle and monitoring the surface of the baffle for particles passing through the baffle which scatter light from the light source. In a preferred embodiment, the surface of the baffle is monitored using an imaging system.

In a first step, the substrate or device containing the substrate is placed into the system of the invention such that the first surface of the substrate and the second surface of the substrate are isolated from one another. If there is a restraining device for the substrate or the device containing the substrate, the substrate or device are appropriately restrained. Where the system contains a seal, the seal is seated to insure isolation of the first surface of the substrate from the second surface of the substrate. If the seal is a bladder based seal, the bladder is expanded to form a seal by increasing the fluid pressure in the bladder. Particles are introduced into the system. They can be introduced into the system predispersed in a carrying fluid or they can be dispersed in the carrying fluid in the system. The particles dispersed in a carrying fluid are then passed through the flow path to the first surface of the substrate. In the embodiment wherein the substrate is disposed in a device, the particles are introduced into the inlet of the device. For a wall flow device the particles are introduced into the open flow passages on the inlet face of the device. A pressure differential is created across the wall of the substrate either by increasing the pressure on the first surface of the substrate or by decreasing the pressure on the second surface of the substrate. The carrying fluid passes through the walls of the substrate and where there are defects the particles pass through the wall. A baffle is disposed (placed) on or adjacent to the surface of the substrate or the exit from the device containing the substrate. Care is taken to arrange the baffle and the angle of the vector at the center of the light from the diffused light source to insure the light from the diffuse light source does not directly contact, or reflect therefrom in a manner which interferes with identifying light scattered by the particles exiting, the substrate or the exit of the device containing the substrate. Diffused light from the diffused light source is directed onto the surface of the baffle. In the embodiment, wherein the substrate is a wall flow filter, light rays should not directly contact the exit face of the wall flow filter having the flow passages in contact with the second surface or reflect from the exit face in a manner which interferes with identifying light scattered by the particles exiting the baffle. The surface of the baffle is monitored for particles passing through the substrate by examining it for the scattering of light off of the particles passing through the baffle. In the embodiment wherein an imaging device is used to prepare images of the surface of the baffle, an operator can monitor the imaging device to determine if particles are passing through the substrate. In one embodiment, an image of the substrate or device exit can be prepared prior to testing and superimposed on an image of the particles exiting the baffle. This can facilitate the identification of the location of the defects. In the embodiment wherein the substrate is a wall flow filter, one goal of the taking an image of particles exiting the wall flow filter is to identify the location of the defects. In this embodiment, the baffle is located on the exit face of the wall flow filter which has the flow passages in contact with the second surface of the wall. Where an image of the exit face of the wall flow filter is superimposed over the image of the particles exiting the baffle, it is relatively easy to identify the particular flow passage having a wall with a defect. The use of a superimposed image is not required to make this identification. For substrates or devices that can be repaired they are repaired at the identified location. For those that cannot be repaired they are discarded as part of a quality control system.

In another embodiment, the invention relates to a method of locating leaks in a substrate, having a first and a second surface wherein the substrate is adapted for preventing the flow of a fluid through the substrate from the first surface to the second surface, wherein the process comprises: a) isolating the first surface from the second surface; b) creating a pressure differential between the first surface and the second surface wherein the pressure on the first surface is higher than the pressure on the second surface; c) contacting the second surface of the substrate or the exit of the device containing the substrate with a baffle comprising a plurality of fluid flow passages wherein the baffle is of a sufficient size to cover the second surface or the fluid exit point of the device containing the substrate and; d) exposing the surface of the baffle to light from a source of diffuse light; e) contacting the first side of the substrate with a carrying fluid containing particles of a particle size that the substrate is designed to retain in the first surface of the substrate; f) monitoring the space immediately above the surface of the baffles for the light scattered by particles that have passed through the substrate.

The first surface of the substrate is isolated from the second surface of the substrate to force a carrying fluid to pass through the wall of the substrate. The surfaces may be isolated within a device in which the substrate is disposed. One method is to form a closed chamber on one side of the substrate or device which is in contact with the first surface of the substrate or the inlet of the device. A pressure differential is created across the wall of the substrate by either increasing the pressure on the first surface of the substrate or by decreasing pressure on the second surface of the substrate. This is discussed in more detail hereinbefore. The baffle is placed in contact with, adjacent to or near the second surface of the substrate or the exit of the device containing the substrate. The carrying fluid having particles dispersed therein is contacted with the first surface of the substrate or with the inlet of the device containing the substrate as described hereinbefore. The pressure differential is chosen to be sufficient to cause the carrying fluid to pass through the wall of the substrate. The particles will be retained on the first surface of the substrate if there are no defects in the wall of the substrate or in the device containing the substrate. If there are defects in the substrate or the device containing the substrate large enough to pass the particles, the particles will pass through the substrate, and where it is part of a device, through the exit of the device. The particles, then pass through the baffle. Diffuse light is directed onto the surface of the baffle as described herein. In a preferred embodiment the diffused light is passed through a lens to focus a majority of the diffused light on the surface of the baffle. The diffused light source and the baffle are arranged to prevent light rays from the diffuse light source from coming into contact with the surface of the substrate or exit of the device or reflecting off of the substrate or baffle in a manner which interferes with monitoring for exiting with particles. This is discussed hereinbefore. The surface of the baffle is monitored for light scattered by particles passing through the baffle. Preferably, this is achieved using an imaging device as described hereinbefore. The location of the defect is preferably identified. In another preferred embodiment the defect is corrected.

In a preferred embodiment the substrate is a wall flow filter. Preferably, the wall flow filter has two opposing faces with a honeycomb structure wherein the honeycomb structure establishes flow passages which pass through the structure from a first end, or face, to a second end, or a face, wherein at a first end of the filter every other passage is sealed in a manner such that fluid cannot flow through the sealed passages and at the second end of the filter the passages not sealed at the first end of the filter are sealed; wherein each passage is sealed at only one end. Preferably, the first surface of the substrate comprises the walls of the wall flow filter having its flow passages in communication with the particles wherein the particles are introduced into the wall flow filter through said passages. Preferably, the baffle is in contact with the end, face, of the honeycomb cylinder which has flow passages open which are not the flow passages to which the particles are introduced.

Figure 2:
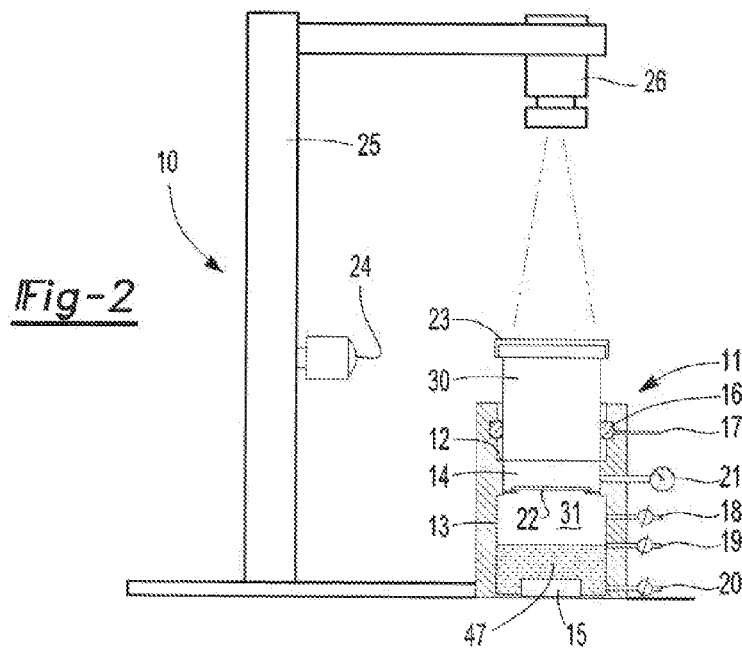
FIG. 2 is a view of a wall flow filter in a defect testing device.

The present invention is illustrated in a number of exemplary embodiments, as discussed with respect to the figures. FIGS. 1 and 2 show the device of the invention 10. FIG. 1 shows a wall flow filter 30 seated in a holder 11. FIG. 2 shows the filter 30 seated in a holder 11 and all of the other elements of the device 10. Shown is a holder 11 for the wall flow filter 30, wherein the filter is placed on a ledge 12 which holds the filter 30 above a chamber 13 which comprises two parts, a chamber wherein the particles and the carrying fluid are mixed 31 and a flow path 14. The mixing chamber 31 and the flow path 14 are separated by a splash guard 22 to prevent water from splashing into the flow path 14. A humidifier or nebulizer 15 is the particle generator. The particles are generated from water 38 in the bottom of the mixing chamber 31. A seal 16 is disposed about the outside wall of the filter 30. The seal 16 has an air inlet 17 for seating the seal 16 about the filter 30. Shown is an air inlet 18 which introduces air as the carrying fluid. Also included is a water inlet 20 and a water outlet 19. The system has a pressure gage 21 for monitoring the pressure in the chamber 13. A baffle 23 is located on the exit face (not shown) of the filter 30. A diffuse light source of an array of light emitting diodes 24 is shown attached to the support structure 25. Attached to an arm of the support structure 25 is an imaging assembly 26 located above the baffle.

In operation, a filter 30 is placed onto the ledges 12 of the holder 11. Air is introduced through the air inlet 17 to seat the seal 16 around the outside wall of the filter 30. The particle generator 15 forms particles from the water 47 located in the bottom of the mixing chamber 31. Air is introduced through the air inlet 18 and water particles and air are mixed in the mixing chamber 31. The mixture of water particles and water are transported into the flow path 14 and then into contact with the first surfaces of flow passages of the filter 30 open to the flow passage 14. A pressure differential is created by introducing pressurized air into to chamber 31 by air inlet 18. The air flows through the walls of the flow passages of the filter 30. The water particles are either retained on the first surface of the walls or pass through defects therein. The particles passing through defects flow through the flow passages in contact with the second surface of the walls out through the baffle 23. The particles exiting the filter scatter light generated by the diffuse light source 24. The imaging assembly 26 takes images of the scattered light from the particles. The images can be used to locate the passage that has a defect and optionally the defect can be repaired.

FIG. 7 is similar to FIG. 2 wherein line 36 shows the plane of the surface of the baffle 23 and line 35 shows the central vector of the cone of diffuse light directed on to the center of the baffle 23. The angle of light Θ 37 is the angle of the respective lines 35 and 36 starting at the center of the baffle 23.

Figures 3, 4:
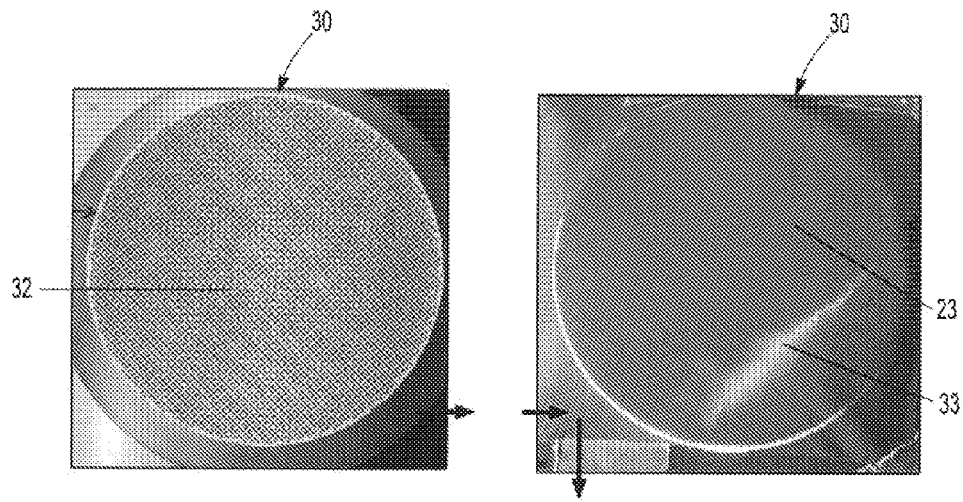
FIG. 3 is a view of the exit face of a wall flow filter.
FIG. 4 is a view of the exit face of a wall flow filter having a baffle disposed thereon which shows the image of the light scattered by water particles exiting the face of the filter.
Figures 5, 6:
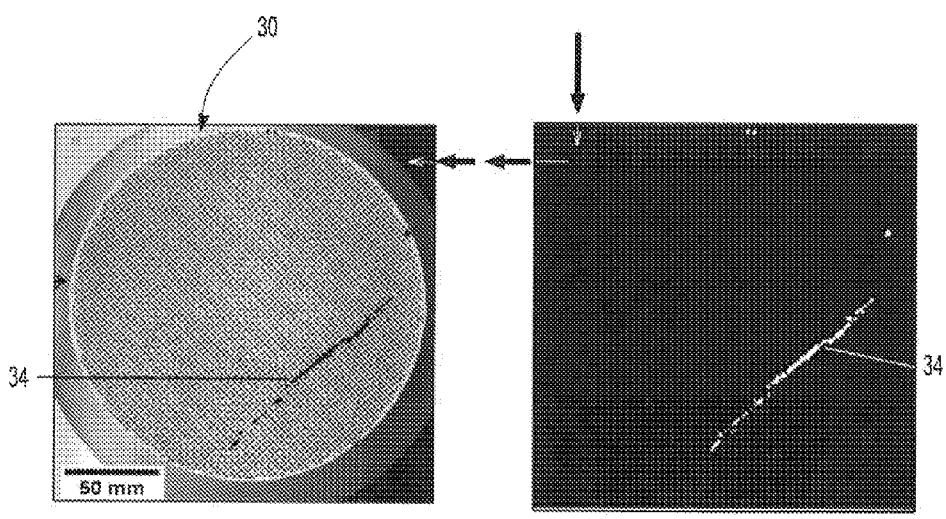
FIG. 5 is an image of the light scattered by the water particles.
FIG. 6 is an image of the light scattered by the water particles superimposed on the exit face of a wall flow filter.

A study of the system of the invention is performed. FIG. 3 to 6 show the results. In the study the apparatus illustrated in the figures is utilized to examine a wall flow filter. From the study, FIG. 3 shows an image of the exit face 32 of the filter 30 is taken by the imaging assembly. The baffle in the form of a mesh 23 is located on the face of the filter 32 and an image taken, this image is not shown. A stream of water particles is introduced into the inlet of the filter 30 and an image of the baffle 23 located on the exit face of the filter 32 is taken, FIG. 4. Shown is the light scattered by the water particles 33. An image analysis of the last image is performed which is an image of the reflection of the water particles 34, see FIG. 5. The result of the image analysis, FIG. 6, is the image of the light scattered by the water particles 34 is superimposed on the image of the fitter face 31 without the baffle located thereon. This allows identification of the defective flow channels.

Figure 8:
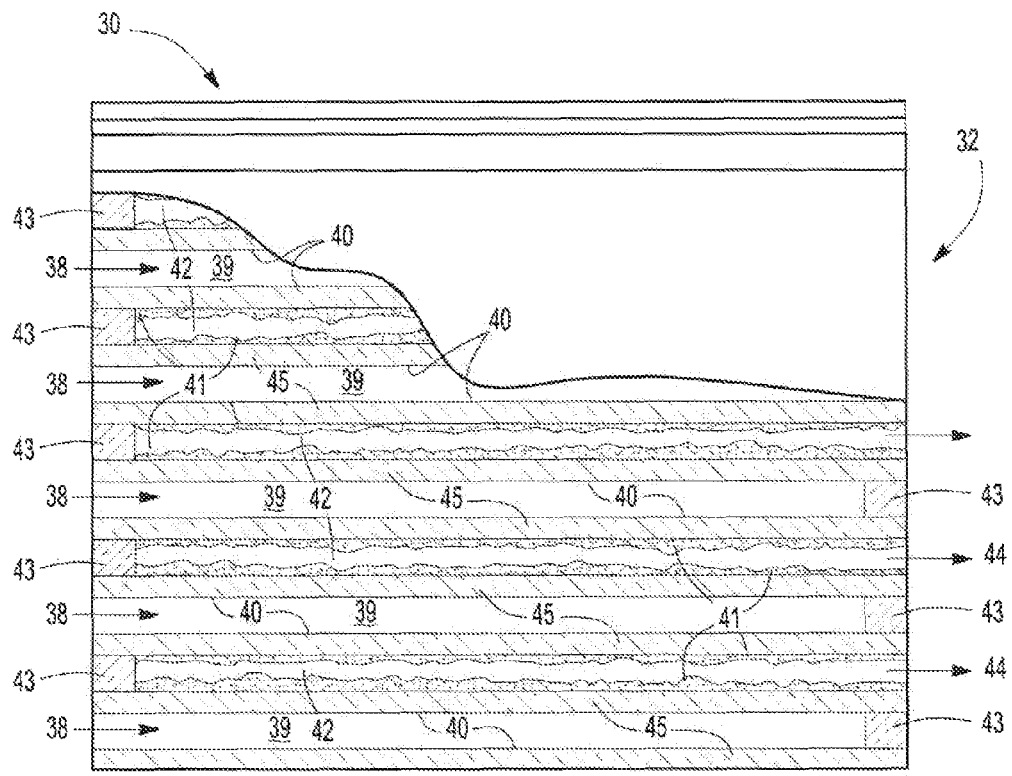
FIG. 8 is a cutaway view of a wall flow filter showing the flow of particulate matter through a defect in a wall of a wall flow filter.

FIG. 8 is a cutaway view of a portion of a wall flow filter 30 through the center of a wall flow filter 30. The wall flow filter 30 has a plurality of walls 45 which form flow passages 39 and 42. Fluid containing particles 33 can be introduced into in-flow passages 39. Fluid which passes through the walls 45 then passes through exit-passages 42 to the exit face 32 of the wall flow filter 30. Arrow 38 shows the flow direction of fluid into the wall flow filter 30. Arrows 44 show the flow of fluid exiting the wall flow filter 30 from the exit face 32. Plugs 43 are disposed at one end of each flow passage 39 and 42. Plugs 43 for the in-flow passages 39 are on the right hand side and plugs for the exit passages 42 are on the left hand side of the drawing. The figure also shows a number of first surfaces 40 of walls 45 (substrate) which are in contact with the in-flow passages 39 and second surfaces 41 in contact with the exit passages 42. Disposed between each pair of first surfaces 40 and second surfaces 41 is a wall 45.

Figure 9:
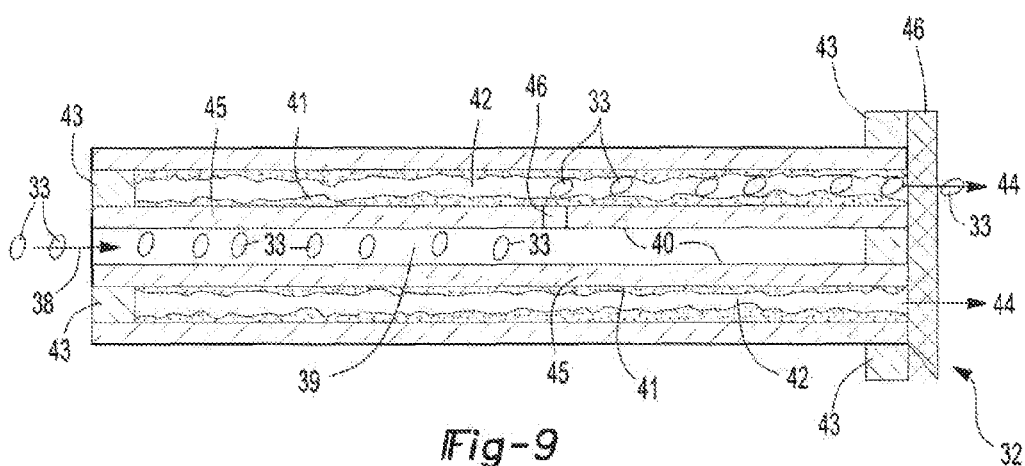
FIG. 9 shows three flow passages of a wall filter and the flow of particles through a defect in one of the walls.

FIG. 9 shows three flow passages 39 and 42 of a wall filter 30. Also shown are plugs 43, one in-flow passage 39 and two adjacent exit passages 42. First surfaces 40 are shown in contact with in the in-flow passage 39 and second surfaces 41 are shown in contact with the exit passages 42. Disposed between the first surfaces 40 and the second surfaces 41 are walls 45. Plugs 43 at the end of the flow passages 39 and 42 are shown. Also shown are a plurality of particles 33 flowing in a fluid into the in-flow passage 39 in the direction as shown by arrow 38. A defect 46 is shown in one wall 45 through which the plurality of particles 33 are passing into the exit passage 42. The particles 33 then flow out of the wall flow filter 30 at the exit face 32 through the baffle 23 in the flow direction shown by arrow 44. The particles 33 would reflect light and identify the passage having a defect 46.

The preferred embodiment of the present invention has been disclosed. A person of ordinary skill in the art would realize however, that certain modifications would come within the teachings of this invention. Therefore, the following claims should be studied to determine the true scope and content of the invention.

Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. Parts by weight as used herein refers to compositions containing 100 parts by weight. The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combination of elements, ingredients, components or steps herein also contemplates embodiments that consist essentially of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

What is claimed is:

1. A system for locating defects in a substrate adapted to separate fluids having at least two surfaces, a first and a second surface, which are isolated from one another and wherein the substrates or devices containing the substrates have an exit point for fluids passing through the substrate, the system comprising:
   a) a particle generator capable of generating particles of a controlled size which is greater than the size of particles which the substrate is adapted to pass from the first surface to the second surface;
   b) a system for creating a pressure differential between the first and the second surface of the substrate;
   c) a light source generating a diffuse cone of light;
   d) a baffle having a plurality of flow passages that particles can pass through;
   e) a closed flow path from the particle generator to the first surface of the substrate; wherein the light source is directed in the direction of the second surface of the substrate or the exit of the substrate, the angle of the direction of the light from the light source, as measured by a vector at the center of the light pattern from the light source in relation to the plane of the second surface of the substrate is between about 2 degrees and about 85 degrees; and
   f.) an imaging device adapted to capture images of light emitted from the light source and reflected from particles gassing from the first surface to the second surface or through the exit of the substrate.

2. A system according to claim 1 which further comprises a structural member adapted to hold the substrate, particle generator, flow path and baffle in a chosen alignment with respect to one another.

3. A system according to claim 1 wherein the system further comprises a seal between the flow path and the substrate to isolate the second surface of the substrate from the particle generator and to maintain the first surface of the substrate in contact with the flow path such that particles generated by the particle generator are in contact with the first surface.

4. The system according to claim 1 wherein the system for creating a pressure differential between the first and second surface of the substrate either increases the pressure in the flow path and thus pressure on the first surface of the substrate or lowers the pressure on the second surface of the substrate.

5. A system according to claim 1 wherein the baffle comprises a wire mesh wherein the pattern of the wires creates flow passages that particles can pass through.

6. A system according to claim 1 wherein the direction of the light as measured by a vector at the center of the light pattern in relation to the plane of the second surface of the substrate is between about 2 degrees and 50 degrees.

7. A system according to claim 1 wherein a lens is located between the light source and the baffle which is adapted to focus the majority of the light generated by the light source on to the surface of the baffle.

8. A method of locating leaks in a substrate or in a device containing the substrate, wherein the substrate has a first and a second surface, and wherein the substrate is adapted for preventing the flow of a fluid through the substrate from the first surface to the second surface or separating components of the fluid, the process comprising:
   a) isolating the first surface from the second surface;
   b) creating a pressure differential between the first surface and the second surface wherein the pressure on the first surface is higher than the pressure on the second surface;
   c) contacting the second surface of the substrate or the exit of the device containing the substrate with a baffle of a sufficient size to cover the second surface, or the exit of the device containing the substrate, the baffle having a plurality of flow passages that particles can pass through;
   d) exposing the surface of the baffle to a diffuse cone of light from a light source;
   e) contacting the first side of the substrate with carrying fluid containing particles of a particle size that the substrate is a designed to retain in the first surface of the substrate;
   f) monitoring the space above the surface of the baffle for light from the light source scattered by particles that have passed through the substrate.

9. A method according to claim 8 wherein the baffle has a plurality of interconnected parts which form a pattern wherein the arrangement of the interconnected parts of the baffle, the thickness of the baffle in the direction perpendicular to the plane of the second surface and the angle of a line drawn through the center of the light pattern generated by the light source in relation to a plane created by the surface of the baffle are chosen such that no direct light rays contact the second surface of the substrate or the exit of the substrate.

10. A method according to claim 8 wherein the surface of the baffle is monitored for the reflection of light from particles by a system capable of capturing an image.

11. A method according to claim 8 further comprising passing the light from the light source through a lens located between the light source and the baffle to focus the majority of the light generated by the light source onto the surface of the baffle.

12. A method according to claim 8 wherein the pressure differential across the substrate is created by applying pressure to the first surface of the substrate.

13. A method according to claim 8 wherein the pressure differential across the substrate is created by applying a vacuum to the second surface of the substrate.

14. A method according to claim 8 wherein the substrate is a membrane or film.

15. A method according to claim 8 wherein the substrate is a wall flow filter.

16. A method according to claim 15 wherein the wall flow filter has two opposing faces and a honeycomb structure wherein the honeycomb structure establishes flow passages which pass through the structure in a direction perpendicular to the two opposing faces wherein at a first face of the filter every other passage is sealed in a manner that fluid cannot flow through the sealed passages and at the second face of the filter the passages not sealed at the first face of the filter are sealed; wherein each passage is sealed at only one face.

17. A method according to claim 16 wherein the first surface of the substrate comprises the walls of the wall flow filter having its flow passages in communication with the particles wherein the particles are introduced into the wall flow filter through said passages.

18. A method according to claim 16 wherein the baffle is in contact with the end of the honeycomb cylinder which has flow passages open which are not the flow passages to which the particles are introduced.

* * * * *